(12) United States Patent
Ihde et al.

(10) Patent No.: US 11,655,446 B2
(45) Date of Patent: May 23, 2023

(54) METHOD FOR USING BIVALVE WASTE AS MEDIA FOR MICRO-ALGAL PRODUCTION

(71) Applicant: Morgan State University, Baltimore, MD (US)

(72) Inventors: Thomas F. Ihde, St. Leonard, MD (US); Rebekah Borgert, Lusby, MD (US)

(73) Assignee: MORGAN STATE UNIVERSITY, Baltimore, MD (US)

( * ) Notice: Subject to any disclaimer, the term of this patent is extended or adjusted under 35 U.S.C. 154(b) by 0 days.

(21) Appl. No.: 17/486,302

(22) Filed: Sep. 27, 2021

(65) Prior Publication Data

US 2022/0098544 A1     Mar. 31, 2022

Related U.S. Application Data

(60) Provisional application No. 63/083,191, filed on Sep. 25, 2020.

(51) Int. Cl.
    *C12N 1/12*     (2006.01)

(52) U.S. Cl.
    CPC ..................................... *C12N 1/12* (2013.01)

(58) Field of Classification Search
    CPC ....................................................... C12N 1/12
    See application file for complete search history.

(56) References Cited

FOREIGN PATENT DOCUMENTS

CN            109349177 A   *  2/2019

* cited by examiner

*Primary Examiner* — Ruth A Davis
(74) *Attorney, Agent, or Firm* — Whitefird, Taylor & Preston, LLP; Peter J. Davis

(57) ABSTRACT

A method for cultivating micro-algae cultures using bivalve waste comprising usable nitrogen and phosphorus as a nutrient source. The micro-algae cultures may be used in turn as a nutrient source for oysters.

7 Claims, 4 Drawing Sheets

METHOD FOR USING BIVALVE WASTE AS MEDIA FOR MICRO-ALGAL PRODUCTION

BACKGROUND OF THE INVENTION

Field of the Invention

The present invention relates to methods for cultivating bivalves.

SUMMARY OF THE INVENTION

Micro-algal production is a vital component of shellfish aquaculture. While vital in shellfish hatchery production, micro-algal supplementation can also be beneficial during broodstock conditioning and juvenile production when food is limiting, or when algae populations in ambient water are not beneficial to the bivalves. Three of the most common algal genera used in shellfish aquaculture, and particularly that of oyster aquaculture, are *Chaeotceros, Isochrysis* and *Tetraselmis*. These algae provide essential nutrients required for growth during the hatchery phase and vary in cell size and composition.

Micro-algal growth in shellfish operations in the United States is a precise operation, with delicate care of the algal stocks and equipment required to ensure pure, clean, cultures. This is crucial for hatchery biosecurity and a healthy crop. Micro-algal production for food is considered an intensive aquaculture practice, requiring large amounts of equipment, sterile conditions, and high amounts of input and labor. Other forms of aquaculture use simple low maintenance and low input mechanisms to increase crop production. One low maintenance/low input way to increase crop production is to use nutrients in the form of biologic material or additives to spur algal growth in ponds, tanks or crop locations, increasing the amount of food available. This in turn, increases crop production. It is often difficult to manage and target specific algal species, and thus, a more intensive form of algal production is used for shellfish. Oysters remove nitrogen, phosphorous, and particulates from the water column, and expel what is not ingested in the concentrated form of feces and pseudofeces. Oysters incorporate 7.86% and 0.82% nitrogen and phosphorus per gram dry tissue weight, respectively.

This invention uses waste (feces and pseudo-feces) harvested from oyster cultures to promote monoculture microalgae production. The overarching goal of the invention is to capture usable nitrogen and phosphorous from oyster waste to cultivate mono-culture algae that can subsequently be used to supplement oyster diets. The removal of waste from the culture system allows for increased food density—resulting in faster growth by reducing the stress of food limitation. Accordingly, the inventors have discovered that oyster waste is a value-added product for land-based systems, reducing feeding costs by supplementing, or may be used to help farms easily culture algae for use in a different life stage, such as a hatchery. According to the invention, investigators assessed the ability to cultivate microalgae cultures using only oyster waste as a nutrient source and compared resulting algal growth to that observed using industry standards for nutrients under the same experimental conditions.

DETAILED DESCRIPTION

Figure 1:
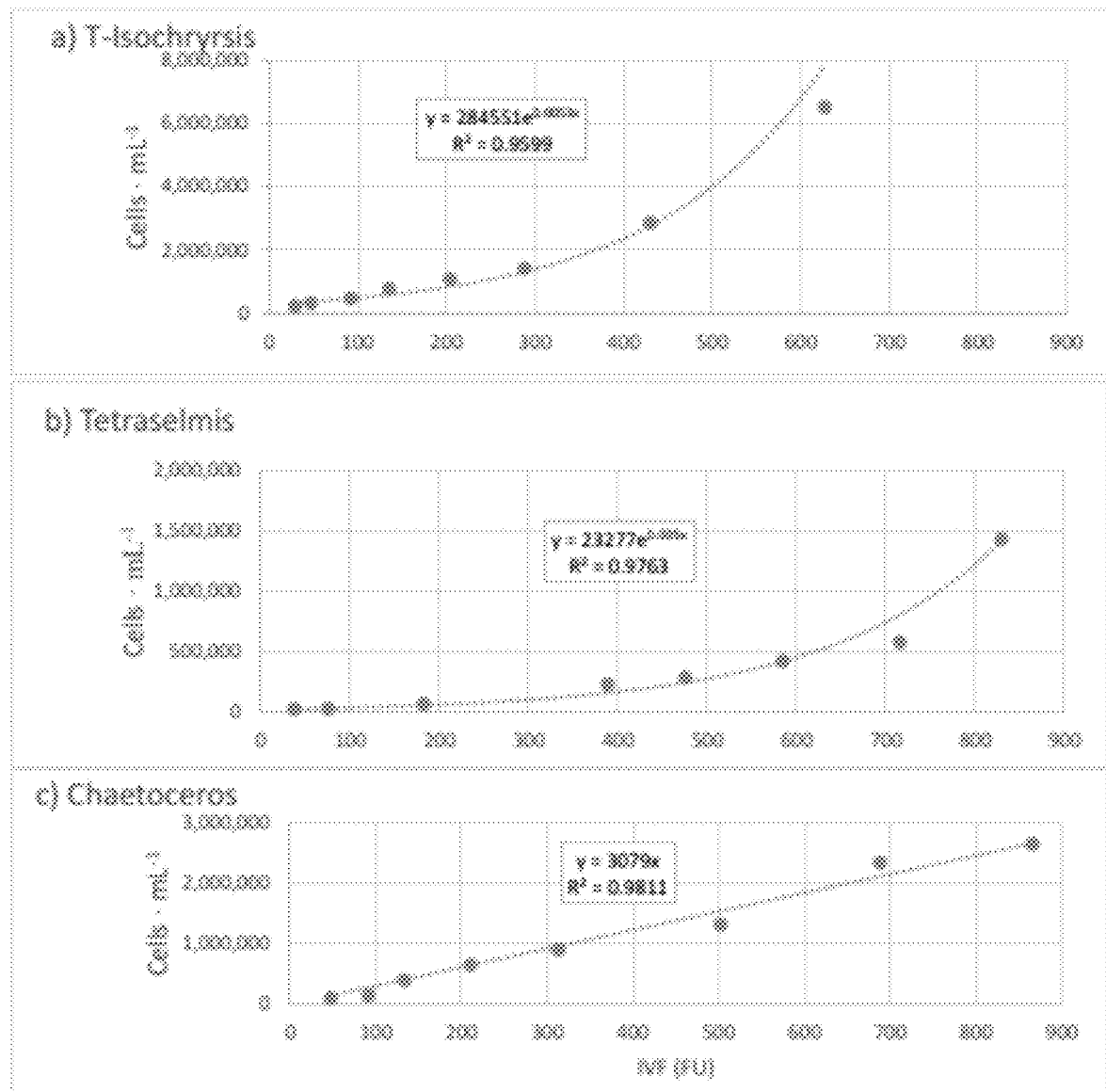
FIG. 1 shows equations developed to convert in vivo fertilization (IVF) Fluorescence Units (FU) to cell density (cells/mL). IVF was measured, and a subsample was preserved with dilute Lugol's solution for later counting on a hemocytometer and compound microscope (100× mag). Equations were chosen based on best fit $R^2$ value for (a) T-*Isochrysis*, (b) *Tetraselmis*, and (c) *Chaetoceros*.

Instant Ocean® seawater salt and tap water were used to create a stock ASW mixture at 13 parts per thousand (ppt). The mixture was held in a conical storage tank and aerated at 24° C. for 24-48 hours before animals were introduced. Adult *Crassostrea virginica* (Eastern Oyster), 2-4" in mean shell length, were collected from Patterson Bar, Patuxent River, Md. Oysters were scrubbed of epifauna using a wire brush and placed in a freshwater bath for 30 minutes to rid the oysters of any encrusting organisms, to ensure there were no additional fouling organisms that could contribute to nutrient waste in the experimental system. The oysters were then passed through a light bleach bath, rinsed, and placed in a refrigerator overnight before being placed in a 150 L recirculating tank with the artificial seawater. After 24 hours, the tank was drained and rinsed to remove any algae, feces, or pseudo-feces that were in the digestive system. The tank was refilled with 13 ppt artificial water from a stock container. Oysters were fed 20 mL of Reed Mariculture 1800 daily. After 7 days, the accumulated wastewater was collected by siphoning the bottom of the tank through a 1 µm filter bag to remove solid waste.

The nutrient water was diluted with the stock ASW to create different concentrations of nutrient water (25%, 50%, and 100%). Two control treatments were also created for the experiment, and included stock ASW, and the current industry standard of L1 media (Guillard and Hargraves 1993; table 1).

TABLE 1

Nutrient analysis of at the start of the project.

| Media | PO4 (mg/L) | NO2 (mg/L) | NO23 (mg/L) | NH4 (mg/L) |
| --- | --- | --- | --- | --- |
| L1 Media | 1.2005 | 0.0008 | 13.8000 | 0.008 |
| 100% Nutrient Water Media | 3.3740 | 0.1147 | 25.4000 | 0.062 |
| 50% Nutrient Water Media | 2.3500 | 0.0592 | 12.6000 | 0.026 |
| 25% Nutrient Water Media | 1.3696 | 0.0294 | 6.6700 | 0.035 |
| Artificial Seawater | 0.0071 | 0.0007 | 0.3580 | 0.014 |

The five resulting media solutions were autoclaved to ensure sterility. Using sterile techniques, 50 ml of nutrient media were placed into acid-washed, 1" diameter 60 ml test tubes. Six replicates were prepared for each of the five treatments (25%, 50%, 100% oyster waste nutrient water, ASW, and L1 media). Silicate was added to all samples growing *Chaetoceros* sp. at $1 \text{ mL·L}^{-1}$. All media was filtered through a 0.3 Millipore filter and 250 ml was sent to Chesapeake Bay Laboratory for nutrient analysis (Table 1).

Stock cultures of *Isochrysis, Chaetoceros* and *Tetraselmis* were cultured in ASW and L1 media (+silicate for diatoms) using Instant Ocean® at 13 ppt salinity. Inoculation cell density was determined during previous pilot studies to achieve an IVF around 15 FU (Table 2).

TABLE 2

Inoculation volumes of stock algae were determined for each species based on a target IVF of 15 FU. The following inoculation volumes were added to each test tube per species.

| Stock Species | Inoculation Volume (μL) | Initial IVF (FU) |
| --- | --- | --- |
| T-Isochrysis | 100 | 17 |
| Chaetoceros | 30 | 4.5 |
| Tetraselmis | 50 | 7 |

The tubes were capped loosely to allow gas exchange and placed in an incubator with light from the top equidistant to all treatment tubes, on a 12:12 light:dark cycle, and kept at 72° C.±0.5° C. Each day, the tubes were tightly capped, inverted, and then shaken using a vortex mixer to ensure media and cells were well-mixed, and measured using a Turner Instruments 10-AU Field and Laboratory Fluorometer. Treatment trays of replicates were rotated daily to control for variation in light exposure.

To convert IVF to cell density, dense stock cultures were diluted with ASW and IVF was measured for each species. The results are expressed in arbitrary units (FU) on the ×1, 3 and 10 sensitivity scale (full scale=1000 units). A subsample of each dilution was preserved with Lugol's solution, and replicate counts were performed manually using a hemocytometer and light microscope. An equation was used to convert IVF to cell density (FIG. 1). IVF readings can vary based on cell size and light adaptation (Butterwick and Talling, 1982). All samples received similar exposure to light and light history prior to sampling. All samples were from the same stock culture, and therefore in the same growth phase. Measurements and/or samples were collected for 26 days in an effort to catch the growth, lag and crash phase of most treatments (Nov. 26, 2018-Dec. 21, 2018). If IVF measurements exceeded the reading capacity of the fluorometer, subsamples were preserved for later direct counts. All IVF samples were converted to cell density for analysis.

Results

Figure 2:
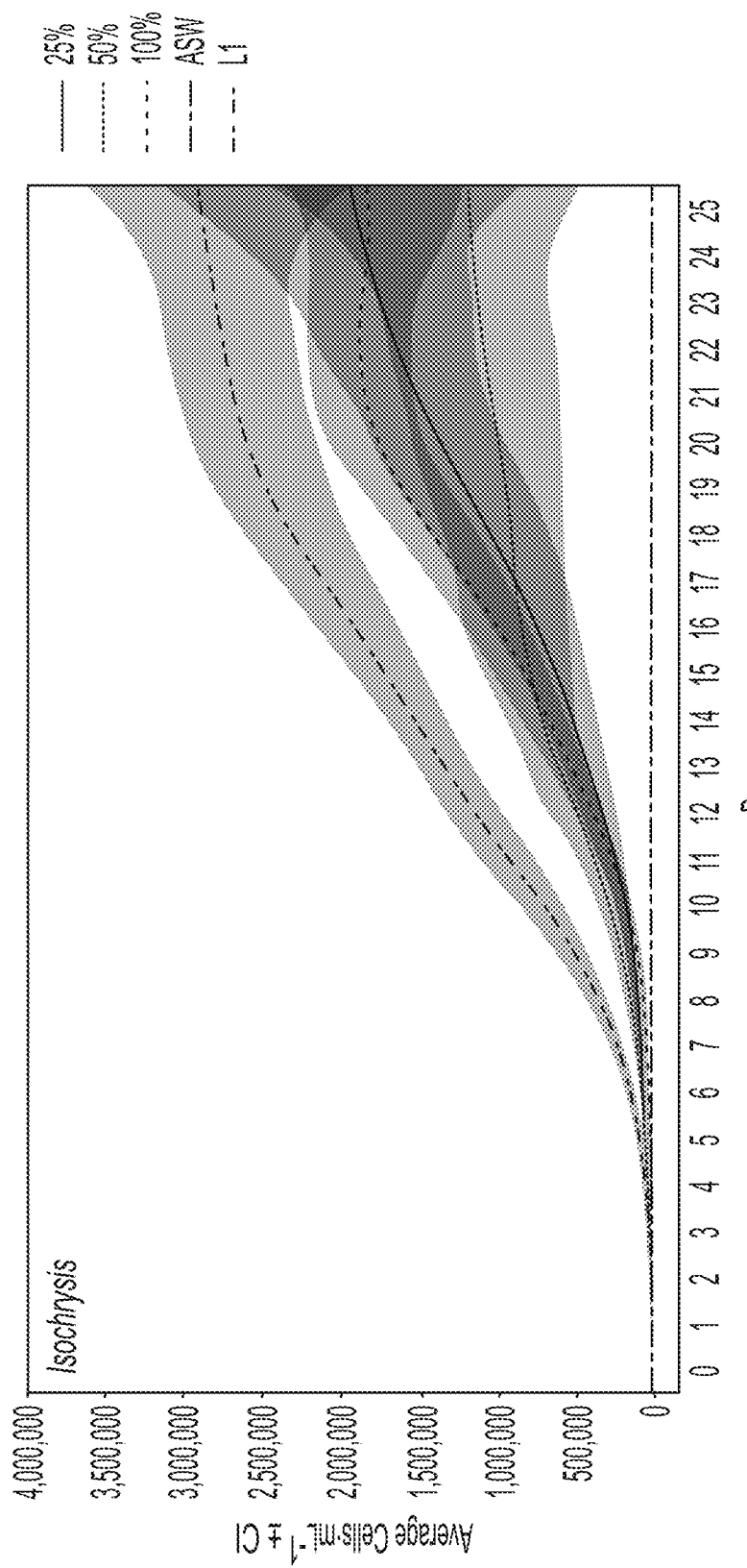
FIG. 2 shows culture growth using 100%, 50% and 25% oyster waste in enriched nutrient water, artificial seawater (ASW) (control), and L1 (industry standard) across three species: a) T-*Isochrysis*, (b) *Tetraselmis*, (c) *Chaetoceros*.
Figure 2:
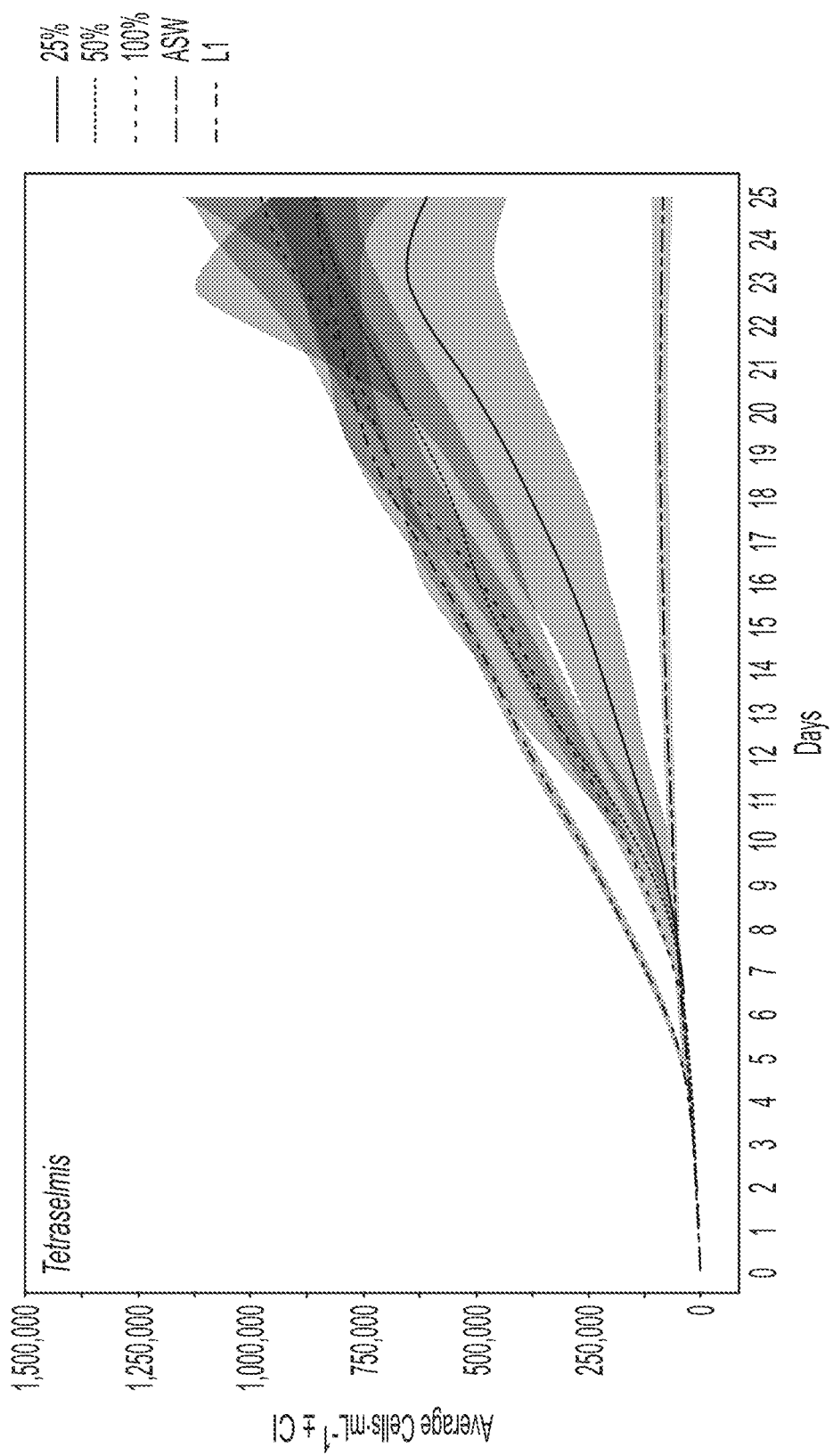
Figure 2:
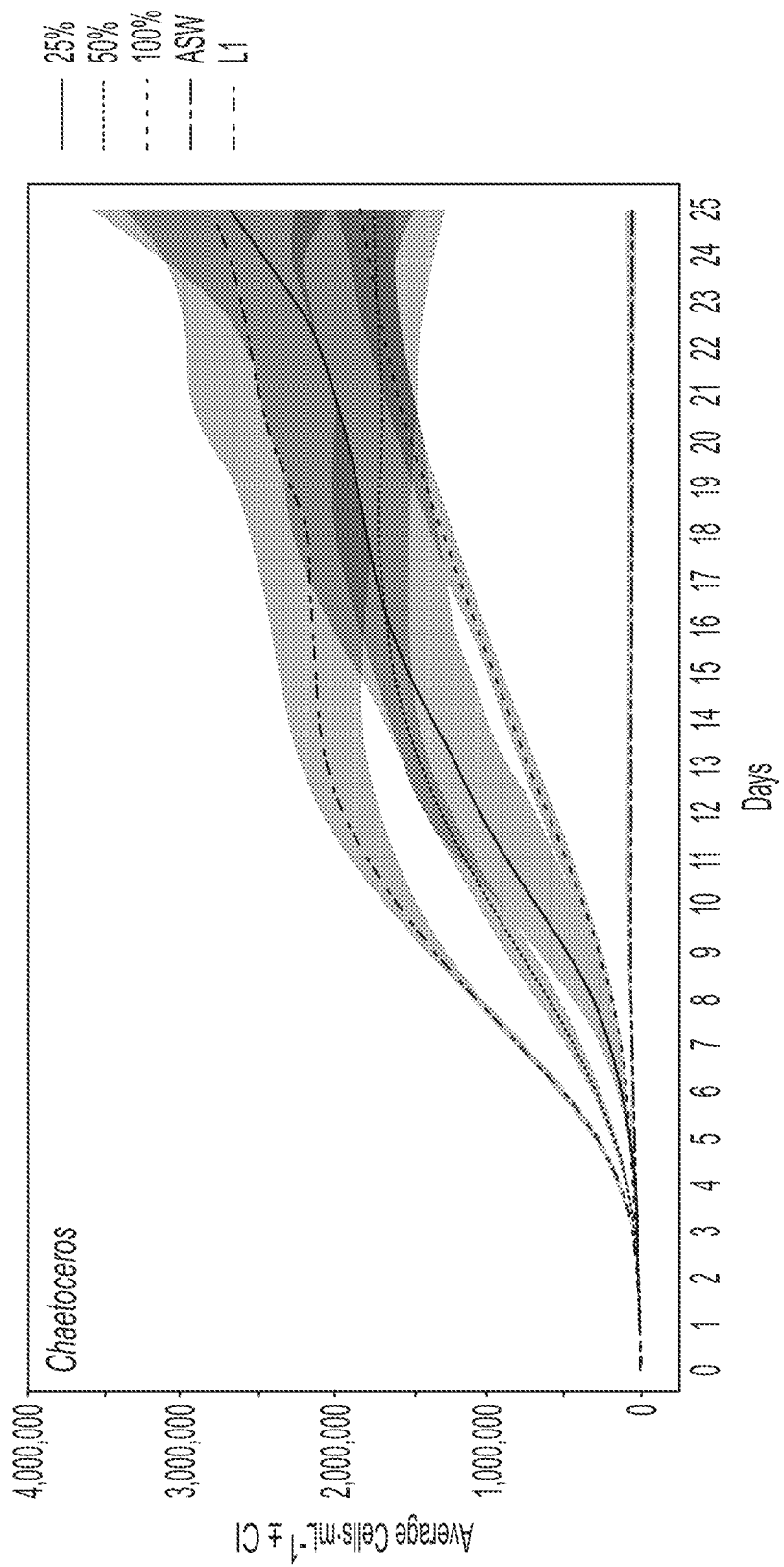

The growth, lag and crash phases of growth were captured for all media types for *Tetraselmis, Chaetoceros* and *Isochrysis* species but did not indicate crashes on all media types (FIG. 2). There was successful growth of all species, indicated by production larger than that of ASW control. In general, L1 performed the best, with 100% nutrient water, with 50% and 25% producing in decreasing amounts, but some species demonstrated faster growth at lower concentrations of oyster nutrients. This is especially clear in the *Tetraselmis* cultures.

Discussion

This work demonstrates that micro-algal species commonly used as food for oyster culture can be grown using oyster waste as a nutrient source. Some algal species (*Chaetoceros* and *Isochrysis* spp.) grew faster (i.e., less lag time) in the short-term with oyster nutrient water than they did with the industry standard L1 solution.

The high R-squared values found in FIG. 1 indicate a high confidence in the conversion of IVF to cell density (0.97-*Tetraselmis,* 0.98-*Chaetoceros,* 0.96-*Isochrysis*). There is, however, a slight discrepancy seen in samples counted manually when cultures exceed the range of the fluorometer and the last converted measurement (typically 900). This is especially common on the *Chaetoceros* species. This species does form chains, and the chains may have made counting difficult. IVF measures chlorophyll-a. While the regressions were very strong during the start of the experiment, it is possible that the amount of chlorophyll in each cell changed as the cells divided and the culture experienced rapid growth and lag growth.

While nutrients were used in all media, the nitrogen to phosphorous ratios vary between media types and are inconsistent between species. The *Isochrysis* had large changes in the amount of nitrogen in the artificial seawater control. It is possible that this culture had bacterial contamination or something affecting the nutrient cycling. All species had large changes between L1 media and nutrient water medias. This most likely indicates that there was a limiting nutrient. The nutrient analysis data needs to be compared to peer-reviewed publications and literature on nutrient uptake in order to fully understand what these changes mean in terms of production and nutrient input.

The experiment is repeated using waste from cultures of Pacific oyster (*Crassostrea gigas*), the Kumamoto oyster (*Crassostrea sikamea*), the European Flat oyster (*Ostrea edulis*) and the Olympia oyster (*Ostrea conchaphila*) to feed *Chaeotceros, Isochrysis* and *Tetraselmis* microalgae cultures, as well as *Chlorella* microalgae cultures, with similar results.

Overall, the evidence shows that oyster waste is a productive nutrient source for algal culture, which can be easily extracted from land-based systems to increase algal production at little to no cost. Five gallons of F/2 algae food by Proline costs approximately $200, and L1 used for smaller batch cultures costs $70 to make 50 L of media. There is a clear economic and environmental advantage to reducing nutrient inputs and reusing oyster waste.

The invention claimed is:

1. A method for promoting micro-algae production comprising harvesting bivalve waster from oysters and adding said bivalve waste to micro-algal cultures, wherein said bivalve waste is harvested from oysters.

2. The method of claim 1, wherein said bivalve waste comprises nitrogen and phosphorus.

3. The method of claim 1, wherein said micro-algae cultures comprise T-*Isochrysis, Tetraselmis,* and/or *Chaetoceros* and/or *Chlorella* cultures.

4. A method for cultivating oysters comprising providing micro-algae cultures to an oyster colony, and harvesting bivalve waste from said oyster colony, wherein said micro-algae cultures are cultivated with said bivalve waste as a nutrient.

5. The method of claim 4, wherein said bivalve waste is harvested from said oyster colony.

6. The method of claim 4, wherein said bivalve waste comprises nitrogen and phosphorus.

7. The method of claim 4, wherein said micro-algae cultures comprise T-*Isochrysis, Tetraselmis,* and/or *Chaetoceros* and/or *Chlorella* cultures.

* * * * *